United States Patent
Zikria et al.

(12)

(10) Patent No.: US 6,207,654 B1
(45) Date of Patent: Mar. 27, 2001

(54) CAPILLARY MEMBRANE STABILIZATION AND REDUCTION OF INFLAMMATION DURING THE COURSE OF CHEMOTHERAPY OR ANTIVIRAL TREATMENT THROUGH THE USE OF BIODEGRADABLE MACROMOLECULES AND INTERLEUKIN-2

(76) Inventors: Bashir Zikria; Jemal D. Zikria, both of 196 Millbrook Cir., Norwood, NJ (US) 07640

( * ) Notice: Subject to any disclaimer, the term of this patent is extended or adjusted under 35 U.S.C. 154(b) by 0 days.

(21) Appl. No.: 08/837,841

(22) Filed: Apr. 22, 1997

Related U.S. Application Data

(60) Provisional application No. 60/016,764, filed on May 3, 1996.

(51) Int. Cl.[7] .......................... A61K 31/00; A61K 38/19
(52) U.S. Cl. ..................... 514/60; 514/2; 514/8; 514/12; 514/59; 514/921; 514/950; 424/85.1; 424/85.2; 536/102; 536/112
(58) Field of Search .............. 514/2, 8, 12, 60, 514/59, 921, 950; 424/85.1, 85.2; 536/102, 112

(56) References Cited

U.S. PATENT DOCUMENTS 4,994,444 * 2/1991 Zikria ...................... 514/60

OTHER PUBLICATIONS

Sagone et al. (1991) Blood, vol. 78, No. 11, pp. 2931–2936, Dec. 1, 1991.*
Berthiaume et al. Am. J. Respiratory Crit Care Med vol. 152, pp. 329–335, 1995.*
Stuntz et al. Lymphology vol. 23, pp. 149–154, 1990.*
Orucevic et al. J. of Immunotherapy. vol. 18, No. 4, pp. 210–220, 1996.*

* cited by examiner

Primary Examiner—Prema Mertz
(74) Attorney, Agent, or Firm—Evelyn M. Sommer

(57) ABSTRACT

There is provided a method of treating a human subject to prevent leakage of serum proteins from capillary endothelial junctions during a period of increased capillary permeability. The method comprises administering to a subject an effective amount of a composition containing hydroxyethyl starch, dextran or hydroxyethyl starch and dextran. The compositions contain these macromolecules in a molecular size and concentration to effectively seal the capillary junctions and stabilize the capillary membranes. The sealant effect is accomplished by a biophysical process due to the adhesiveness and configuration of the macromolecules, and because of their size. There is also provided a means of treating viral and other bacterial infections and cancer, by introducing into the composition of polysaccharide(s) a biological agent, preferably interleukin-2. In certain instances of viral infections associated with human cancers it may be possible to prevent the appearance of malignancy by pretreating with these compositions. In addition other agents, antioxidants, may be included in these compositions.

12 Claims, No Drawings

CAPILLARY MEMBRANE STABILIZATION AND REDUCTION OF INFLAMMATION DURING THE COURSE OF CHEMOTHERAPY OR ANTIVIRAL TREATMENT THROUGH THE USE OF BIODEGRADABLE MACROMOLECULES AND INTERLEUKIN-2

Reference is made to Provisional Application Ser. No. 60/016,764 filed May 3, 1996.

The present invention relates to a method for treating human subjects to prevent leakage of macromolecules from capillary endothelial junctions as a consequence of extremely severe and life threatening side effects due to cancer biological therapy for cancer, infectious diseases, septic shock, and in viral infections implicated in human cancers. More particularly this invention relates to a method for preventing leakage of macromolecules from capillary endothelial junctions during a period of increased capillary permeability secondary to cytotoxicity of biological agents used to treat cancer, infectious diseases, (bacterial and viral) and to provide antiviral therapy in viral infections implicated in human cancers, as an approach to improving the immune response of cancer patients as well as preventing the inflammatory processes set into play during treatment with other anticancer drugs, radiation and as a consequence of the numerous infections that cancer patients acquire as a result of being immunologically compromised.

The invention comprises the use of compositions containing a single polysaccharide or a combination of two polysaccharides for the prevention of leakage from capillary endothelial junctions of macromolecules. The compositions comprise in addition to one or two polysaccharides, a biological agent preferably interleukin-2 or interferon.

The polysaccharide(s) for inclusion in the compositions of the invention include hydroxyethyl starch (HES, hetastarch, Hespan®) and dextran. The protective action of these polysaccharides has been found by the inventor to be brought about by a biophysical/biochemical process resulting in membrane stabilization of the capillary endothelial cell by virtue of the "sealing" effects as well as capillary membrane stabilization brought about by these molecules.

Current scientific literature reveals that inflammatory mediators initiate a biochemical chain of events that increase capillary permeability and deteriorate capillary membrane stability. These mediators include pharmacologically active amines such as histamine and 5-hydroxytryptamine, polypeptides such as bradykinin, kallikrein and leukotoxine, the prostaglandins, and various complements including derivatives thereof. These mediators act specifically on the junction of the endothelial cells of capillaries so that the junctions cannot contain colloids such as serum albumin within the vessel. The serum albumin escapes into the interstitium creating a nonfunctional "third space", the volume of which increases proportionally to albumin leakage and the presence of cytokines as well as proteolytic enzyme activity within the matrix. This leakage further widens capillary membrane-transport between the circulatory system and the functional cells resulting in cellular anoxia, cellular energy deficit, acidosis and possibly leads to sequential organ failure.

In the past, the problem of albumin leakage and the concurrent creation of a third space has been approached through pharmacological means. The present invention approaches the problem as a biophysical phenomenon by utilization of natural or synthetic polysaccharides (macromolecules) as sealants and capillary membrane stabilizers to prevent or substantially reduce the escape of albumin and other molecules through the junction of the endothelial cells of the capillaries as well as stabilize the colloidal oncotic pressure. This is accomplished by virtue of the configuration and biophysical/biochemical properties (adhesiveness) of the utilized polysaccharides.

Hydroxyethyl starch (Hespan U.S. Pat. No. 3,523,938) is an artificial colloid derived from a waxy starch, composed almost entirely of amylopectin. The branched amylopectin polymer has a degree of polymerization on the order of several hundred glucose residues. The segments between the branched points average about 25 glucose residues linked by alpha-D-(1–4) glucosidic bonds, while the branched points are linked by alpha-D-(1–6) bonds. Hydroxyethyl ether groups are introduced into the glucose units of the starch and the resultant material is hydrolyzed. Clinical hetastarch is characterized by its molecular weight and its degree of substitution. The average molecular weight is approximately 480,000 daltons with a range of 400,000 to 500,000 and with 80% of its polymer units falling within the range of 30,000 to 2,400,000 daltons. The molar substitution is 0.7 which means hetastarch has 7 hydroxyethyl groups for every 10 glucose units. The polymerized glucose units in hetastarch are joined primarily by 1–4 linkage with hydroxethyl groups being attached primarily at the number 2 position. The polymer closely resembles glycogen. The degree of branching is approximately 1:20 which means that there is one 1–6 branch for every 20 glucose units. The chemical name for hetastarch is hydroxyethyl starch. The structural formula is as follows:

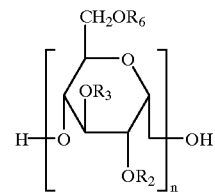

Amylopectin derivative in which $R_2$, $R_3$, and $R_6$ are H or $CH_2CH_2OH$, or $R_6$ is a branching point in the starch polymer connected through a 1–6 linkage to additional α-D-glucopyranosyl units.

The colloidal properties of 6% hetastarch approximate those of human albumin. Intravenous infusion of HES results in expansion of the plasma volume slightly in excess of the volume infused but which decreases over the succeeding 24–36 hours. This expansion of plasma volume improves the hemodynamic status of the subject for 24 hours or longer. Hydroxyethyl starch molecules below 50,000 daltons are rapidly eliminated by renal excretion with approximately 40% of a given total dose appearing in the urine in 24 hours. The hydroxethyl group is not cleaved by the body, but remains intact and attached to the glucose units when excreted. Significant quantities of glucose are not produced (metabolism) as hydroxyethylation prevents complete metabolism. Despite its extensive clinical use hetastarch has not been observed to act in a way more than merely exerting a colloidal oncotic pressure when compared to albumin.

Hydroxyethyl starch is administered by intravenous infusion only. In adults the amount usually administered is 500 to 1500 mls. Doses of 1500 mls per day of 6% hydroxyethyl starch per 70 kg man have been used in postoperative open heart operations and trauma patients. Hydroxyethyl starch can be delivered in 0.9% saline, 5% dextrose or Ringer's lactate.

The inventors have utilized other polysaccharides in addition to hetastarch and have produced promising results. These polysaccharide macromolecules include glycogen and dextran.

Glycogen is a readily mobilized storage form of glucose. It is a very large polymer of glucose residues. Most of the glucose residues are linked by alpha-1–4 glycosidic bonds of which there is one in about 10 residues. Glycogen granules are 100 to 400 Angstrom and have a molecular weight range of about 270,000 to 350,000 daltons. The molecules of glycogen do not have a unique size. The average molecular weight is several hundred kilodaltons.

Dextran, another polysaccharide is made up of glucose residues only, mainly in alpha-1–6 linkage. Occasional branches are formed by alpha-1–2, alpha-1–3 or alpha-1–4 linkages. The nature of the linkages are dependent on the source of the dextran. Certain bacteria secrete dextran as a by-product of their growth and commercial dextran is manufactured by bacterial culture procedures. By varying the growth conditions of the bacteria, the molecular weight of the dextran can be controlled to bring about the desired size. Useful molecular weights for plasma substitution range from 100,000 to 500,000. Dextran of appropriate molecular size does not pass through the capillary pores and therefore, can replace plasma proteins as colloid osmotic agents.

Few toxic reactions have been observed when using either dextran or hetastarch for fluid replacement therapy.

The capillary wall is composed of a unicellular layer of endothelial cells and is surrounded by a basement membrane. The thickness of the wall is about 0.5 micron. The diameter of the capillary is 4 to 9 microns. The endothelial cells of the capillary wall are held apart approximately 6 to 7 nanometers (60 to 70 Angstroms) by pore-like structures. Most water-soluble ions and molecules pass between the interior and exterior of the capillary through these pores. Such substances include sodium and chloride ions, glucose etc. If a substance is lipid-soluble, it can diffuse directly through the cell membranes without having to pass through the pores. Such substances include oxygen and carbon dioxide. The pores in the capillaries of some organs have special characteristics to meet the special needs of the organs. For example in the brain, the junctions between the capillary endothelial cells are in the main "tight" junctions that will allow only very small molecules to pass into the brain tissue. This is the so called blood-brain barrier. In the liver, the pores between the capillary endothelial cells are very wide so that almost all dissolved substances present in the plasma, including the plasma proteins can pass from the blood into the liver tissue. The pores of the intestinal membranes are midway between those of the muscles and the liver. The width of the capillary intercellular pores, 6 to 7 nanometers is about 20 times the diameter of the water molecule, which is the smallest molecule that normally passes through the capillary pores. On the other hand, the diameters of plasma protein molecules are slightly greater than the width of the pores. Other substances, such as sodium ions, chloride ions, glucose, and urea have intermediate diameters. The permeability of the capillary pores for different substances varies according to their molecular weights.

In the past decade both DNA and RNA viruses have been implicated in human cancers, examples include: Hepatitis B virus and heptaocellular carcinoma, human papilloma virus and cutaneous and genital carcinoma, Epstein Barr and Burkitt's lymphoma etc.

Over the past few years, many biological agents and many approaches to biological therapy for cancer and infections (AIDS) have been investigated. Presently a range of biological agents is being researched. These include biological response modifiers that may or may not have a direct antitumor effect but are able to stimulate the immune system and so indirectly affect tumors and infectious agents. Among these many biological agents are:

The Interferons—There are several interferons. The 3 major types are alpha, beta and gamma. Alpha and beta form the type 1 class of interferons and Interferon gamma is a type 11. These interferons have overlapping but clearly distinctive biological activities. Interferon-alpha was the first of the cytokines shown to have an antitumor effect, both a direct effect and indirect effect through inducing a more active immune system as a result of their activities in modulating the host immune response. Interferon-alpha has limited activity in renal cell carcinoma and melanoma and has been shown to have a major effect in hairy cell leukemia and in chronic myelocytic leukemia. Interferon-alpha is also occasionally effective in non-Hodgkin's lymphoma and in some people with AIDS who develop Kaposi's sarcoma. The alpha interferons have also been used in treating patients with bladder cancer, cervical cancer, multiple myeloma, and mycosis fungoides.

Interferons also have antiviral activity. Studies are now being done with interferon-beta and interferon-gamma, both of which have similar antitumor and antiviral effects. The interferons have been shown to have marked activity in halting the progression of multiple sclerosis by increasing the interval between attacks as well as preventing infections in individuals with chronic granulomatous disease. All the interferons are being evaluated in combination with other cytokines, or in combination with chemotherapy. The exact mechanism that makes interferons effective is not known . The interferons are produced by activated T cells. They are polypeptides and have a molecular weight of 20,000 to 25,000 daltons. Interferons may be used as natural products (fibroblasts) or as compounds produced by recombinant DNA techniques. The interferons are commercially available.

Interleukins—There are several interleukins (IL-1 through IL-13). Interleukin-1 (IL-1) is a polypeptide produced by macrophages, other cells of the immune system, including T cell, and some tissue cells. IL-1 acts to stimulate the growth and activation of B cells as well as to be involved in the chain of events leading to the release of interleukin-2 (IL-2). Of all the interleukins IL-2 has been most intensively studied. IL-2 increases the activity of lymphocytes. Such activated lymphocytes are called lymphokine-activated killer cells and they are very effective in destroying tumor cells. IL-2 is a polypeptide containing 133 amino acids and some carbohydrate and has a molecular weight of about 15,000 daltons. The source of IL-2 is the T cell. IL-2 has shown effectiveness in treatment of cancer (kidney cancer and melanoma).

IL-2 has been shown to function in varied physiologic systems. For example major burn injury depresses T-cell activation at the level of the IL-2 gene transcription, whereas IL-2 receptor expression and function remain normal. T-cell proliferation can be restored to normal levels by exogenous IL-2. IL-2 infusions have been shown to effectively raise CD4 counts in patients with HIV infection.

IL-6 activity is related to IgA antibody responses.

IL-10 has regulatory functions on a number of cytokines including IL-1, IL-2, IL-8 and tumor necrosis factor. IL-10 has been shown to have a direct effect on the expression of the human elastin gene in vivo and in vitro. This up-regulatory effect on the elastin gene expression indicates the direct effect of IL-10 on connective tissue metabolism.

IL-12 is implicated in the development of Th1 cells. It may have uses in the treatment of cancer, AIDS and infectious diseases both as therapeutic agents and in vaccines.

IL-13 and IL-4 have deactivating effects on inflammatory monocyte functions. Pretreatment of monocytes with IL-13 decreases HIV-1 infection whereas IL-4 increases it. These two interleukins have divergent effects on HIV expression in monocytes.

The other interleukins are active in stimulating B cells and thus antibody production. During antigen driven immune responses, antigen-specific naive B lymphocytes undergo a cascade of events including activation and differentiation into either antibody secreting plasma cells or memory B cells. These events are called immunopoiesis. B cells stimulated with cytokines such as IL-2, IL-4, IL-10 and IL-13 undergo limited proliferation and differentiation into immunoglobulin secreting cells.

Examples of other biological agents include Colony-stimulating factors, Tumor necrosis factors and T cells.

T Cells—Some investigators are studying the use of T cells rather than less specific cells in the fight against cancer. The T lymphocyte recognizes tumor cells and either makes helper factors that stimulate the rest of the immune system or makes killer factors that destroy tumor cells. Killer T cell are a subset of T cells. They can directly kill invading micro-organisms. They are antigen specific and can kill repeatedly. They contain on their surface receptors for IL-2 and are activated by reacting with IL-2.

The compositions of this invention will comprise one or two of the polysaccharides (hydroxyethyl starch and/or dextran) and preferably Interleukin-2 or Interferon as the biological agent, most preferably interleukin-2. An antioxidant such as superoxide dismutase, catalase, glutathione peroxidase, vitamin C, cyclic adenosine monophosphate etc. can be added to the compositions. The mechanism of action of interleukin-2 is known, it is commercially available and it is effective against tumor cells as well as infectious agents. The biologic agents, IL-1, IL-2, and T cells act together as follows: a foreign antigen is present and a macrophage will phagocytose it. The macrophage displays a piece of the invading antigen on its surface. Some helper and killer T cells come along. These helper and killer T cells recognize the macrophage as Self and its displayed antigen as Not-Self. They fix to the to the antigen site on the macrophage The macrophage begins to secrete IL-1, the first chemical messenger in the sequence. IL-1 triggers the mature helper T cell to change into an effector or activated helper T cell. The activated T cell begins to divide making identical copies, clones, of itself. It also starts releasing IL-2. Meanwhile the mature killer T cell has also bound to the macrophage and antigen. This causes the killer T cell to develop IL-2 receptors on its surface. The IL-2 released by the activated helper T cells activates the killer T cell to divide and produce clones of itself. The IL-2 continues to be produced stimulating the succeeding generations of killer T cell clones. This continues until the killer T cells have destroyed the invading antigen. Once the infected cells are all gone, the IL-2 receptors begin to disappear from the surface of the T cells. The killer T cells stop growing and dividing and die.

Most of the cytokines cause fever, fatigue, chills and a skin rash. They induce changes in blood pressure, usually decreasing it. IL-1 and tumor necrosis factors cause general malaise. IL-2 can give rise to extremely severe and life-threatening side effects. IL-2 causes the peculiar capillary leak syndrome. Symptoms include drop in blood pressure and difficulty in breathing. Tissues become edematous (enlarged third space) as fluid and proteins accumulate and there are toxic effects on the heart. Unless treatment is discontinued at this stage, IL-2 may cause kidney shutdown or respiratory arrest and death.

The importance of the compositions, hydroxyethyl starch and IL-2, hydroxyethyl starch dextran and IL-2, and dextran and IL-2 in the treatment of cancer, infectious diseases, and septic shock as well as in alleviating the toxicity of the IL-2 is readily apparent.

The applicants have prepared the following compositions of polysaccharide macromolecules and IL-2 and utilized them in order to inhibit or prevent capillary leakage and reduce inflammation during the course of chemotherapy or antiviral treatment. The procedures carried out by the applicant have shown the following : reduction of the inflammatory reaction, reduction of damage to endothelial cells and other tissues, and enhancement of microcirculatory dynamics, reduction or avoidance of the side effects of IL-2, and thus being able to continue therapy until the viral infection is cleared or the tumor is eliminated. These effects are realized as a consequence of the biophysical/biochemical properties of the polysaccharide molecules as endothelial membrane stabilizers and by positively effecting the osmotic balance between the intra (capillaries) and extra vascular space (interstitium). The antiviral and anticancer activity of IL-2 is both specific and nonspecific, in that it nonspecifically boosts the immune response resulting in the liberation of biologically active factors that increase the reaction of the host to invading organisms or tumor cells and specifically in activating biological factors and cells that are specifically able to recognize and eliminate the specific agent or cell responsible for the pathology.

The total molecular weight range and composition of the invention may differ due to the fact that these macromolecules characteristically exhibit a wide range of molecular weights. The molecular weight ranges of the macromolecules used may also be varied depending on the specific clinical application.

Solutions of the macromolecules are prepared in 0.9% saline, 5% dextrose or Ringer's lactate, Ringer's lactate being the preferred carrier. The amount of the polysaccharide macromolecules in the compositions may vary but essentially range between 3–50% but 6% is the preferred concentration. The exact volume to be introduced intravenously is dependent on the specific clinical entity to be treated and the body weight of the subject. The usual volume is about 500 to 1500 mls however 1500 mls of 6% hydroxyethyl starch can readily be given to a 70 kg man over a 24 hour period (20 ml/kg). When the macromolecules are used in combination the total volume infused is similar to that used for a macromolecule. The sum of the weight of macromolecules in the composition would be in the range of 3–50% and preferably between 6–12%, that is a total of 3–6 grams per 50 ml. Thus the composition would contain 1.5–3.0 grams of each of the component macromolecules per 50 ml if two are used in a 1:1 mixture. If used in a 4:1 mixture (hydroxyethyl starch:dextran) hydroxyethyl starch would be used as 2.4–4.8 grams to 0.6–1.2 gram of dextran per 50 mls.

Solutions of the polysaccharide molecules will be made up in either 0.9% saline, 5% dextrose or Ringer's lactate. The usual volume given by intravenous injection is 500 to 1500 ml and contains about 6 to 12% polysaccharide macromolecules. The amount of a single macromolecule when used would be 3–6 grams per 50 ml and the molecular size utilized would depend on the clinical condition dictating its use.

The amount of IL-2 to be incorporated into a 50 ml intravenous injection would be 100,000–500,000 units/kg. The amount of IL-2 used clinically for immuno-stimulation is 100,000 units/kg every 8 hours. For use in treatment of renal carcinoma or metastatic melanoma 720,000 IU/kg every 8 hours for 15 doses/cycle. Two cycles constitute a treatment course. Such treatment can be repeated as the protocol for the specific clinical condition dictates.

Antioxidants can be included in these compositions. The preferred antioxidants include, superoxide dismutase 5000–20,000 IU/kg; glutathione peroxidase 5–50 units/ml per treatment or 200–400 mg/kg; catalase 5000–12,500 IU/kg/treatment; and vitamin C 2–2.5gr/70 kg man.

The compositions are prepared using either 6 or 12% hydroxyethyl starch or 6–12% Dextran again dependent on the clinical indications. The polysaccharide macromolecules and IL-2 are always introduced intravenously. Treatment can be repeated as indicated.

Examples of some compositions are given in the following table. The following examples are given in order to illustrate the invention and are not to be construed as limitative thereof.

Compositions

| Polysaccharide | grams/20 ml | antioxidant and biologicasl agent | concentration | |
|---|---|---|---|---|
| Hetastarch | 1.2 | superoxide dismutase + | 5000–20,000 | IU/kg |
|  |  | interleukin-2 | 200,000 | IU/kg |
| Hetastarch | 1.2 | vitamin C + | 40 | mg/kg |
|  |  | interleukin-2 | 250,000 | IU/kg |
| Hetastarch | 0.6 | interleukin-2 | 250,000 | IU/kg |
| Dextran | 0.6 |  |  |  |
| Hetastarch | 1.2 | glutathione peroxidase + | 150 | units/kg |
|  |  | vitamin C + | 35 | mg/kg |
|  |  | interleukin-2 | 300,000 | IU/kg |
| Hetastarch | 0.6 | catalase + | 10,000 | IU/kg |
| Dextran | 0.6 | interleukin-2 + | 250,000 | IU/kg |
|  |  | glutathione peroxidase | 200 | units/kg |
| dextran40 | 1.2 | interleukin-2 | 500,000 | IU/kg |
| Hetastarch | 1.2 | superoxide dismutase + | 10,000 | IU/kg |
|  |  | vitamin C + | 35 | mg/kg |
|  |  | interleukin-2 | 500,000 | IU/kg |
| Hetastarch | 1.2 | Catalase + | 12,000 | IU/kg |
|  |  | Interleukin-2 | 300,000 | IU/kg |

The present invention provides a method of treating a human subject to prevent leakage of serum proteins from capillary endothelial junctions during a period of increased capillary permeability. The method comprises administering intravenously to a subject an effective amount of a composition containing hydroxethyl starch, dextran or hydroxyethyl starch and dextran The compositions contain the macromolecules in a molecular size and concentration to effectively seal the capillary junctions and stabilize the capillary membranes. The sealant effect is accomplished by a biophysical process due to the adhesiveness and configuration of the macromolecules, and because of their size. The invention also provides a method of treating viral and other bacterial infections and cancer, by introducing into the composition of polysaccharide(s) a biologically active agent, preferably IL-2. The compositions are administered intravenously in combination with a pharmaceutically acceptable liquid carrier. In certain instances of viral infections associated with human cancers it may be possible to prevent the appearance of malignancy by pretreatment with these compositions.

It is possible in accordance with the invention to administer the hydroxyethyl starch alone or in admixture with dextran prior to the treatment with interleukin-2 or to administer them simultaneously.

We claim:

1. Method of treating human subjects to prevent leakage of macromolecules from capillary endothelial junctions as a consequence of severe life threatening side effects due to cancer, biological therapy for cancer, infectious diseases and septic shock which comprises intravenously administering to a subject in need of such treatment an effective amount of composition comprising 1) a member selected from the group consisting of hydroxyethyl starch, dextran and mixtures thereof and 2) a member selected from the group consisting of interferon and an interleukin selected from the group consisting of IL-2, IL-6, IL-10, IL-12 and IL-13 in a pharmaceutically acceptable liquid carrier therefor.

2. Method according to claim 1 wherein said composition additionally contains at least one antioxidant selected from the group consisting of superoxide dismutase, catalase, glutathione peroxidase, vitamin C and cyclic adenosine monophosphate.

3. Method according to claim 1 wherein said liquid carrier is a member selected from the group consisting of 0.9% saline, 5% dextrose and Ringer's lactate.

4. Method according to claim 1 wherein said polysaccharide is dextran.

5. Method according to claim 1 wherein said polysaccharide is present in said composition in an amount of about 3 to about 50%.

6. Method according to claim 1 wherein said second member is interleukin-2.

7. Method according to claim 6 wherein said interleukin-2 is administered in an amount of about 100,000 to 720,000 units/kg of subject.

8. Method according to claim 1 wherein said polysaccharide is present in an amount of about 6 to about 12%.

9. A composition comprising a member selected from the group consisting of hydroxyethyl starch, dextran and mixtures thereof and a member selected from the group consisting of interferon and an interleukin selected from a group consisting of IL-2, IL-6, IL-10, IL-12 and IL-13 in a pharmaceutically acceptable liquid carrier therefor.

10. A composition according to claim 9 additionally containing at least one antioxidant selected from the group consisting of superoxide dismutase, catalase, glutathione peroxidase, vitamin C and cyclic adenosine monophospate.

11. A composition according to claim 9 comprising hydroxyethyl starch and interleukin-2.

12. A composition according to claim 9 comprising dextran and interleukin-2.

* * * * *